US011964063B2

(12) United States Patent  
Yang et al.

(10) Patent No.: US 11,964,063 B2  
(45) Date of Patent: Apr. 23, 2024

(54) TOWEL DISINFECTION DRYER

(71) Applicant: SHENZHEN ANTOP TECHNOLOGY CO., LTD, Shenzhen (CN)

(72) Inventors: Ruidian Yang, Shenzhen (CN); Weixin Ni, Shenzhen (CN)

(73) Assignee: SHENZHEN ANTOP TECHNOLOGY CO., LTD, Shenzhen (CN)

( * ) Notice: Subject to any disclaimer, the term of this patent is extended or adjusted under 35 U.S.C. 154(b) by 718 days.

(21) Appl. No.: 17/123,497

(22) Filed: Dec. 16, 2020

(65) Prior Publication Data

US 2022/0096672 A1 Mar. 31, 2022

(30) Foreign Application Priority Data

Sep. 25, 2020 (CN) .......................... 202022147642.8  
Oct. 16, 2020 (CN) .......................... 202022317806.7  
Oct. 16, 2020 (CN) .......................... 202022318527.2

(51) Int. Cl.
| | |
|---|---|
| *A61L 2/10* | (2006.01) |
| *A61L 2/14* | (2006.01) |
| *A61L 2/26* | (2006.01) |
| *F26B 3/04* | (2006.01) |
| *F26B 3/28* | (2006.01) |

(52) U.S. Cl.  
CPC .................. *A61L 2/10* (2013.01); *A61L 2/14* (2013.01); *A61L 2/26* (2013.01); *F26B 3/04* (2013.01); *F26B 3/283* (2013.01); *A61L 2202/11* (2013.01); *A61L 2202/122* (2013.01); *A61L 2202/26* (2013.01)

(58) Field of Classification Search  
CPC ..... A61L 2/10; A61L 2/14; A61L 2/26; A61L 2202/11; A61L 2202/122; A61L 2202/26; F26B 3/04; F26B 3/283; F26B 21/001; A47K 10/06  
USPC ......................................................... 34/276  
See application file for complete search history.

(56) References Cited

U.S. PATENT DOCUMENTS

| | | | |
|---|---|---|---|
| 2004/0149936 A1* | 8/2004 | Schweitzer ............... | A61L 2/10 |
| | | | 250/504 R |
| 2020/0330640 A1* | 10/2020 | Funamori ................. | F24F 8/30 |
| 2021/0361792 A1* | 11/2021 | Kraft ...................... | H01J 61/523 |

FOREIGN PATENT DOCUMENTS

| | | | | |
|---|---|---|---|---|
| CN | 107334412 A | * | 11/2017 | |
| CN | 108903749 A | * | 11/2018 | ............. A47K 10/06 |
| CN | 112021977 A | * | 12/2020 | |

\* cited by examiner

*Primary Examiner* — John P McCormack  
(74) *Attorney, Agent, or Firm* — SOROKER AGMON NORDMAN PTE LTD

(57) ABSTRACT

The present application provides a towel disinfection dryer, comprising a main machinery, wherein the main machinery comprises a housing, an ultraviolet light source installed in the housing, a reflector arranged above the ultraviolet light source, a heater installed in the housing, and a fan installed in the housing, the reflector is installed in the housing, the bottom of the housing is provided with a window exposing the ultraviolet light source, and the bottom of the housing corresponding to the outlet of the fan is provided with an air outlet, the heater is arranged on the airflow path of the fan, the reflector defines one or more airflow holes, and the reflector is arranged on the airflow path of the fan.

20 Claims, 12 Drawing Sheets

TOWEL DISINFECTION DRYER

CROSS-REFERENCE TO RELATED APPLICATIONS

The present application claims the priority to the Chinese Patent Application NO. 202022147642.8, filed at the China National Intellectual Property Administration on Sep. 25, 2020 and entitled "towel disinfection dryer", the entire content of which is incorporated herein by reference in its entirety.

The present application claims the priority to the Chinese Patent Application NO. 202022318527.2, filed at the China National Intellectual Property Administration on Oct. 16, 2020 and entitled "Towel disinfection machine", the entire content of which is incorporated herein by reference in its entirety.

The present application claims the priority of the Chinese Patent Application NO. 202022317806.7, filed at the China National Intellectual Property Administration on Oct. 16, 2020 and entitled "Negative ion disinfection machine", the entire content of which is incorporated herein by reference in its entirety.

BACKGROUND

Technical Field

The present application relates to the field of dryers, more specifically, relates to a towel disinfection dryer.

Description of Related Art

The statements here only provide background information related to the present application, and do not necessarily constitute prior art. Towel disinfection dryer is generally used to disinfect and dry towels, clothing and other fabrics. The current towel disinfection dryer generally installs an ultraviolet light source and a heater in the main machinery to irradiate and heat the towel on the rack for disinfection and drying. However, this kind of towel disinfection dryer consumes a lot of energy, and when the ultraviolet light source is working, heat accumulates, resulting in a short life of the ultraviolet light source.

SUMMARY

The purpose of the embodiments of the present application is to provide a towel disinfection dryer to solve the problem of large energy consumption and short life resulted from the accumulation of heat by the ultraviolet light source of the towel disinfection dryer in the related technology.

In order to achieve the above purpose, the technical solution adopted in the embodiments of the present application is to provide a towel disinfection dryer, including a main machinery, the main machinery including a housing, an ultraviolet light source installed in the housing, and a reflector arranged above the ultraviolet light source, a heater installed in the housing, and a fan installed in the housing, the reflector is installed in the housing, and the bottom of the housing is provided with a window exposing the ultraviolet light source, the bottom of the housing corresponding to the way out of the fan is provided with an air outlet, the heater is provided on the airflow path of the fan, the reflector defines one or more airflow holes, and the reflector is provided on the airflow path of the fan.

The beneficial effect of the towel disinfection dryer provided by the embodiment of the present application lies in: compared with the prior art, the towel disinfection dryer of the present application is provided with a reflector to increase the utilization rate of light emitted by the ultraviolet light source, and the reflector is provided on the fan's air intake path, and an airflow hole is provided on the reflector, the airflow will enter the fan through the reflector and then be blown out, which can cool the ultraviolet light source and improve the service life of the ultraviolet light source, and the heat generated by the ultraviolet light source can heat the airflow at the fan inlet to improve energy utilization and reduce energy consumption by utilizing.

BRIEF DESCRIPTION OF THE DRAWINGS

In order to more clearly explain the technical solutions in the embodiment of the present application, the following will briefly introduce the drawings that need to be used in the embodiment or exemplary technical description. Obviously, the drawings in the following description are only the some embodiments of the present application, for those of ordinary skilled in the art, other drawings can be obtained based on these drawings without creative work.

In which, the main reference symbols of the drawings in the figure: 100—Towel disinfection dryer; 10—Main machinery; 11—Housing; 110—Control panel; 111—Bottom plate; 112—Cover; 1121—Buckle; 1122—Trunking; 113—Air outlet; 114—Window; 115—Air inlet; 116—Opening; 117—Optical aperture; 12—Heater; 121—Heating plate; 122—Cooling fin; 13—Fan; 131—Fan cover; 132—Tubular wind turbine; 133—Electrical machinery; 14—Ultraviolet LED module 1; 141—Base plate; 142—ultraviolet LED bead; 15—Ventilation window; 151—Accommodating slot; 161—Lampholder; 162—UV tube; 163—Reflector; 1631—Supporting plate; 1632—Reflective side plate; 1633—Airflow hole; 164—Turnplate; 1641—Rotary disk; 1642—Pivot; 1643—Deck; 165—Supporting seat; 166—Grilling window; 17—Ultraviolet LED module 2; 18—Emitter head; 181—Negative ion release brush; 182—Holder; 183—Guide plate; 20—Rack.

DETAILED DESCRIPTION

In order to make the technical problems to be solved, technical solutions, and beneficial effects by the present application clearer, the present application will be described in further detail below with reference to the accompanying drawings and embodiments. It should be understood that the specific embodiments described here are only used to explain the present application, and are not used to limit the present application.

The reference to "one embodiment", "some embodiments" or "embodiments" described in the present application specification means that one or more embodiments of the present application include the specific features, structures or characteristics described in combination with the embodiment. Therefore, the words "in one embodiment", "in some embodiments", "in some other embodiments", appearing in different places in this specification do not necessarily refer to the same embodiment, but mean "one or more embodiments but not all embodiments", unless otherwise specifically emphasized. In addition, in one or more embodiments, specific features, structures, or characteristics may be combined in any suitable manner.

The abbreviation of LED stands for Light Emitting Diode.

Figure 1:
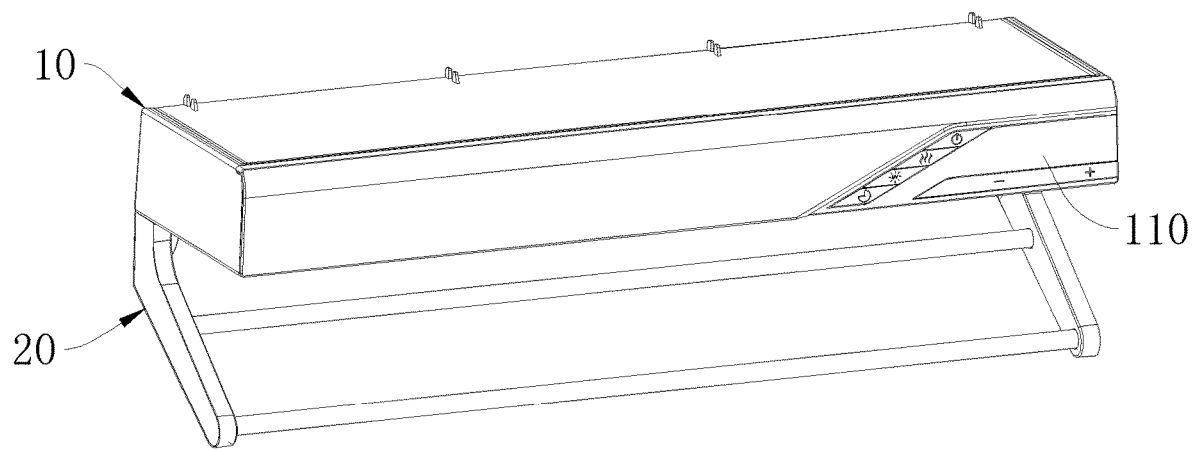
FIG. 1 is a first schematic diagram of the towel disinfection dryer provided by the first embodiment of the present application.
Figure 3:
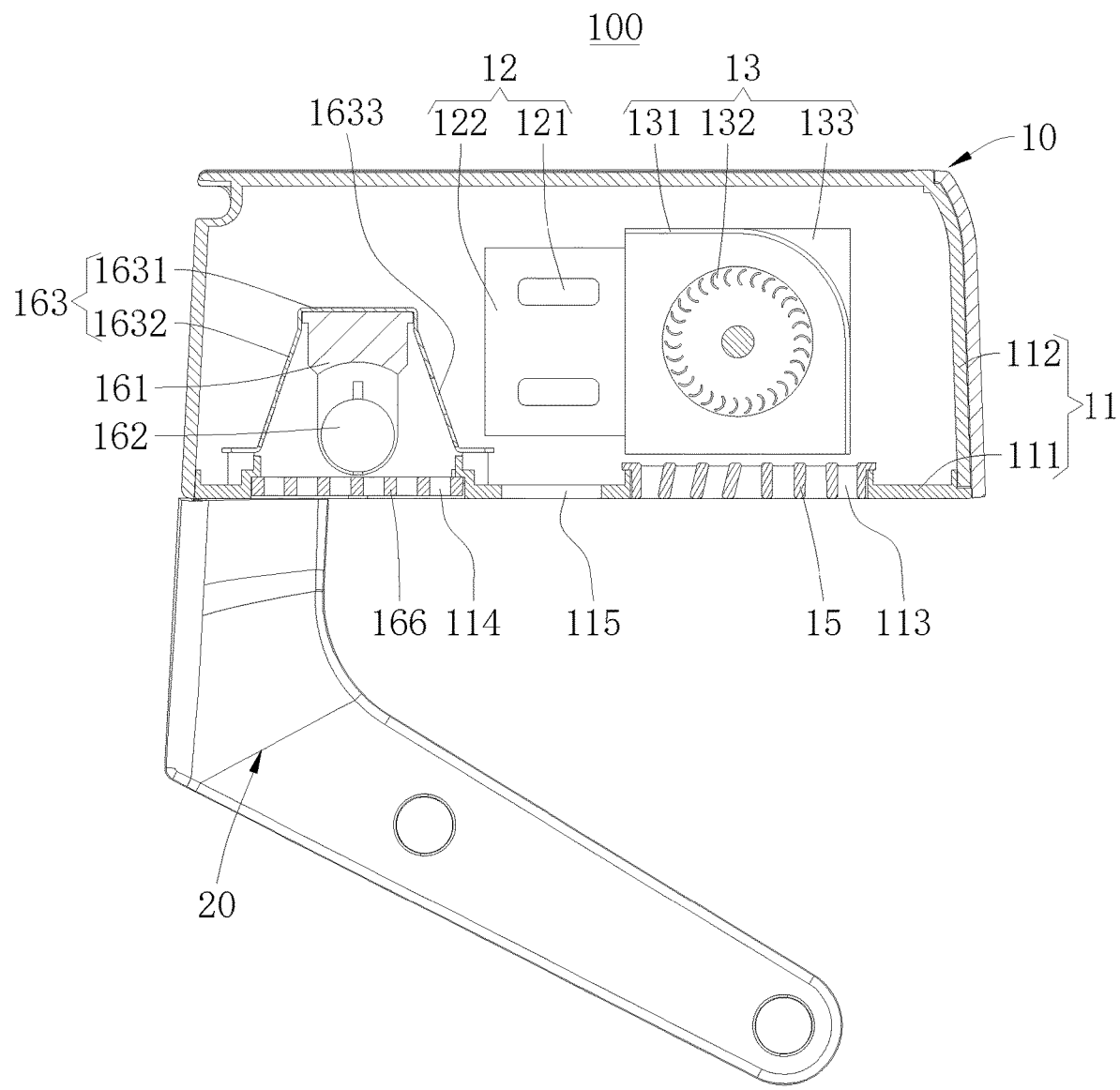
FIG. 3 is a schematic cross-sectional view of the towel disinfection dryer provided by the first embodiment of the present application.

For the convenience of description, please refer to FIG. 1 and FIG. 3. The definition in the present application: when main machinery 10 is installed on the wall, the sides of main machinery 10 close to the wall are main machinery 10, housing 11 and the back side of the towel disinfection dryer 100, and the side of main machinery 10 far away from the wall is main machinery 10, housing 11 and the front side of the towel disinfection dryer 100.

Please refer to FIG. 1 to FIG. 3, the towel disinfection dryer 100 provided by the present application will now be described. The towel disinfection dryer 100 includes a main machinery 10 and a rack 20, wherein the rack 20 is used to hang fabric pieces, that is, fabric pieces such as towels can be hung on rack 20, and main machinery 10 is set above rack 20 to heat, dry and disinfect the fabric pieces on rack 20 through main machinery 10. The rack 20 can be supported at the bottom of the housing to integrate rack 20 and main machinery 10 to facilitate installation and use. Of course, in some embodiments, rack 20 can also be setup separately to install rack 20 and main machinery 10 on the wall, respectively. In some other embodiments, the towel disinfection dryer 100 may also only include the main machinery 10, which is installed above the existing rack 20 in the room.

Figure 4:
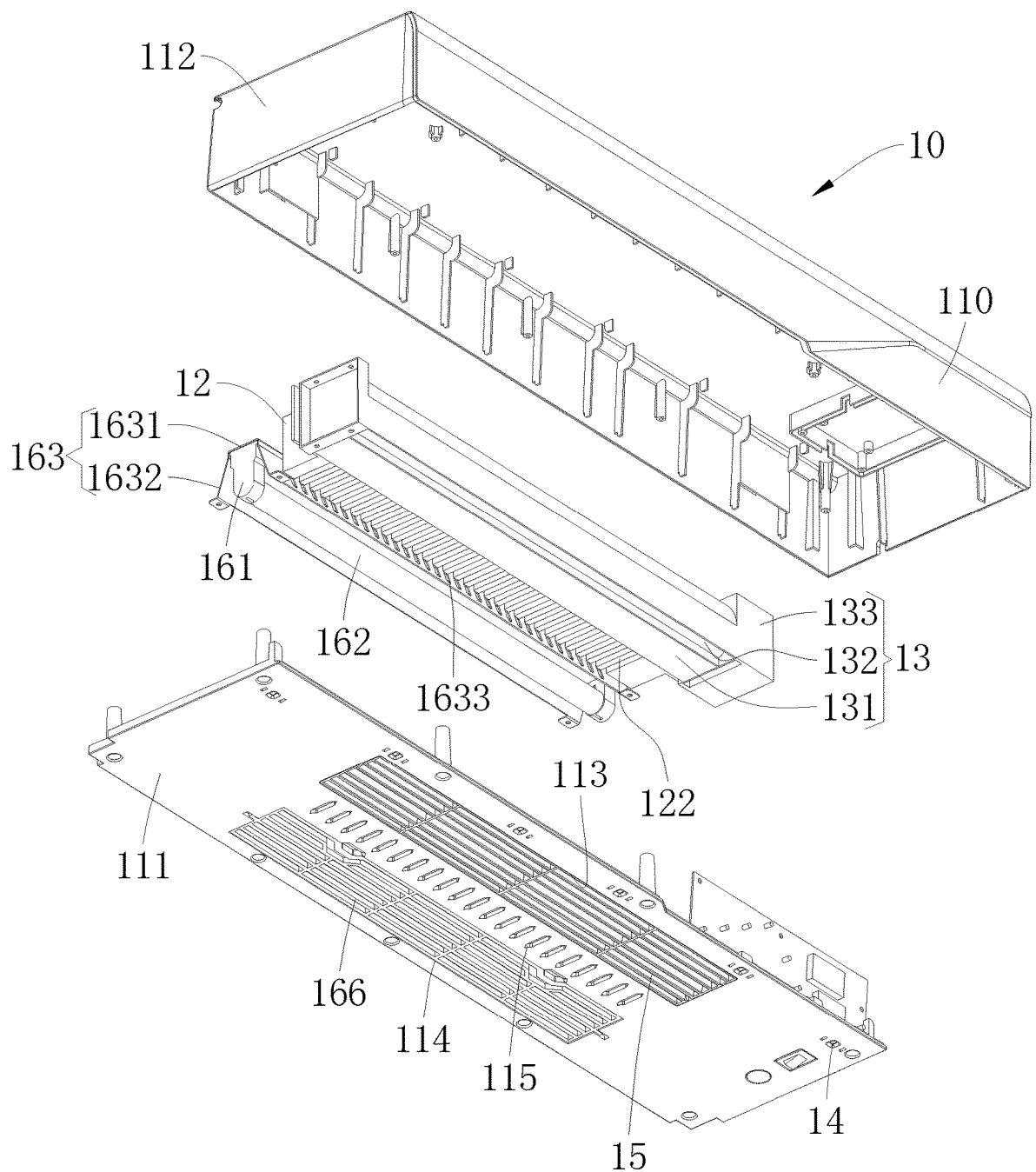
FIG. 4 is a schematic diagram of the exploded structure of the main machinery in FIG. 3.

Please refer to FIGS. 3 to 4, the main machinery 10 includes housing 11, ultraviolet light source, reflector 163, heater 12 and fan 13. Ultraviolet light source, reflector 163, heater 12 and fan 13 are installed in housing 11, and ultraviolet light source, reflector 163, heater 12 and fan 13 are protected by housing 11. The heater 12 is provided on the airflow path of the fan 13, the heater 12 is used to heat the air, and the fan 13 blows out the heated air to dry the cloth. The ultraviolet light source emits ultraviolet light to disinfect the cloth. The reflector 163 can cover the ultraviolet light source partially to reflect the ultraviolet light emitted by the ultraviolet light source to the specified direction, so as to improve the utilization of ultraviolet light, so as to be more energy-saving, and can avoid the ultraviolet light emitted by the ultraviolet light source from irradiating the other parts of the housing 11 to age the corresponding parts. A window 114 and an air outlet 113 are arranged at the bottom of the housing 11, and the window 114 is located at a position corresponding to the reflector 163 to expose the ultraviolet light source, so that the ultraviolet light emitted by the ultraviolet light source can be irradiated out. The air outlet 113 is located at the outlet of fan 13 in order to blow out the airflow. The reflector 163 is located on the intake path of the fan 13, and an airflow hole 1633 is arranged on the reflector 163, so that the air enters the reflector 163 through the window 114, and then enters the fan 13 from the airflow hole 1633, so that the ultraviolet light source in the reflector 163 can be cooled to improve the service life of the ultraviolet light source. And after the air enters the reflector 163, the air will be heated by the ultraviolet light source, so that the heat generated by the ultraviolet light source can be used to further improve energy utilization and reduce power consumption.

Compared with the prior art, the towel disinfection dryer 100 provided by the present application is provided with a reflector 163 to increase the utilization rate of the light emitted by the ultraviolet light source. The reflector 163 is arranged on the air intake path of fan 13, and airflow hole 1633 is arranged on reflector 163, the airflow will enter fan 13 through reflector 163, and then be blown out, which can cool the ultraviolet light source and improve the service life of ultraviolet light source, and the heat generated by ultraviolet light source can heat the air flow entering into fan 13 to improve energy utilization and reduce energy consumption.

Figure 2:
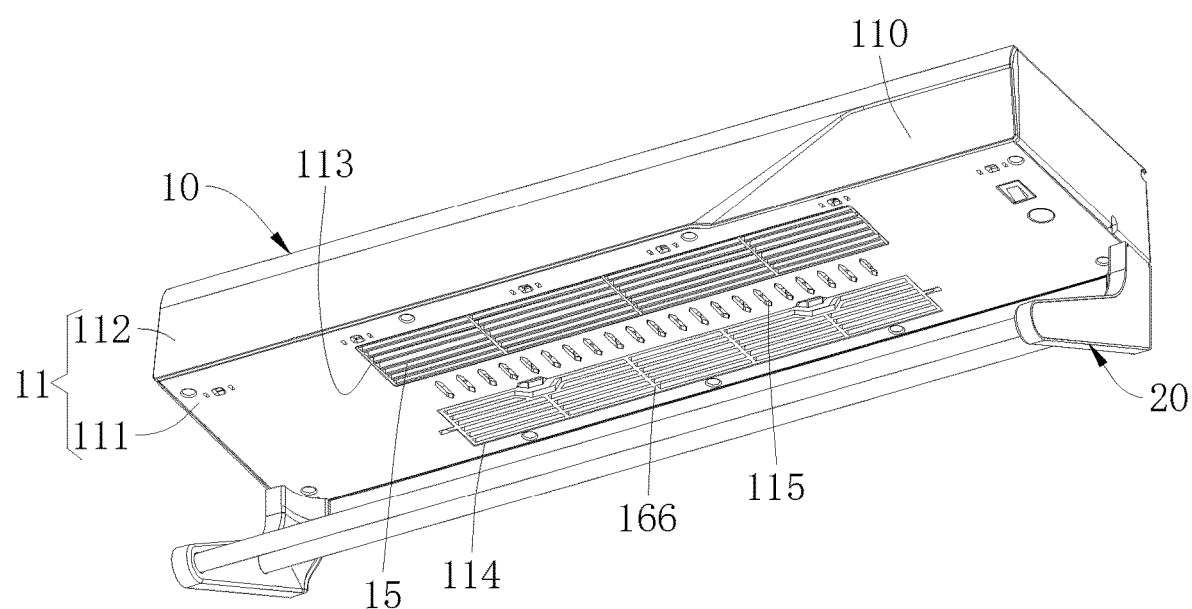
FIG. 2 is a second schematic diagram of the towel disinfection dryer provided by the first embodiment of the present application.

In one embodiment, referring to FIGS. 1 to 3, the housing 11 includes a bottom plate 111 and a cover 112 covering the bottom plate 111, and a window 114 and an air outlet 113 provided on the bottom plate 111. The housing 11 is easy to process and make, and it is also convenient to install the ultraviolet light source, reflector 163, heater 12 and fan 13 in the housing 11. Of course, in other embodiments, the housing 11 can also be formed by combining multiple plates.

In one embodiment, a control panel 110 is provided on the front side of the housing 11, and the control panel 110 is inclined from top to bottom toward the rear of the housing 11 to facilitate user operations and also facilitate the user to determine the position of the control panel 110. In one embodiment, the control panel 110 is provided on the cover 112 to facilitate processing.

Please refer to FIGS. 3 to 4, the ultraviolet light source is UV tube 162, the main machinery 10 also includes a lampholder 161, the lampholder 161 is installed in housing 11, and the lampholder 161 is protected by housing 11. The UV tube 162 is installed on the lampholder 161, and the UV tube 162 is supported by the lampholder 161, and power is supplied to the UV tube 162 so that the UV tube 162 emits ultraviolet light, thereby sterilizing the cloth. The reflector 163 is arranged above on the lampholder 161, and when the UV tube 162 is installed on the lampholder 161, the reflector 163 can cover the UV tube 162 partially to reflect the ultraviolet light emitted by the UV tube 162 to the specified direction, improving the utilization rate of the ultraviolet light for more energy saving. And the reflector can prevent the ultraviolet light emitted by the UV tube 162 from irradiating other components in the housing 11 and aging the corresponding components. In other embodiments, the ultraviolet light source may also be an ultraviolet LED module 1. The ultraviolet LED module 1 includes a base plate and an ultraviolet LED bead installed on the base plate. In some other embodiments, the ultraviolet light source can also be an ultraviolet LED strip.

In one embodiment, the window 114 is located at the position corresponding to the rear side of the bottom of the housing 11, so that when in use, the window 114 is closer to the wall, so the UV tube 162 is also closer to the wall to better limit the range of ultraviolet light and improve safety.

In one embodiment, referring to FIGS. 3 to 4, the heater 12 may be arranged at the entrance of the fan 13, and the air is heated by the heater 12, and then sucked and accelerated by the fan 13 and then being blown out. Due to the relatively small air flow rate at the inlet of fan 13, the gas can be fully heated by heater 12 first, and then enter the fan 13, the heat utilization rate is high, and the corresponding heater 12 power can be made lower. In other embodiments, the heater 12 may also be arranged at the outlet of the fan 13, and the air flow blown by the fan 13 is heated by the heater 12 before flowing out.

Figure 5:
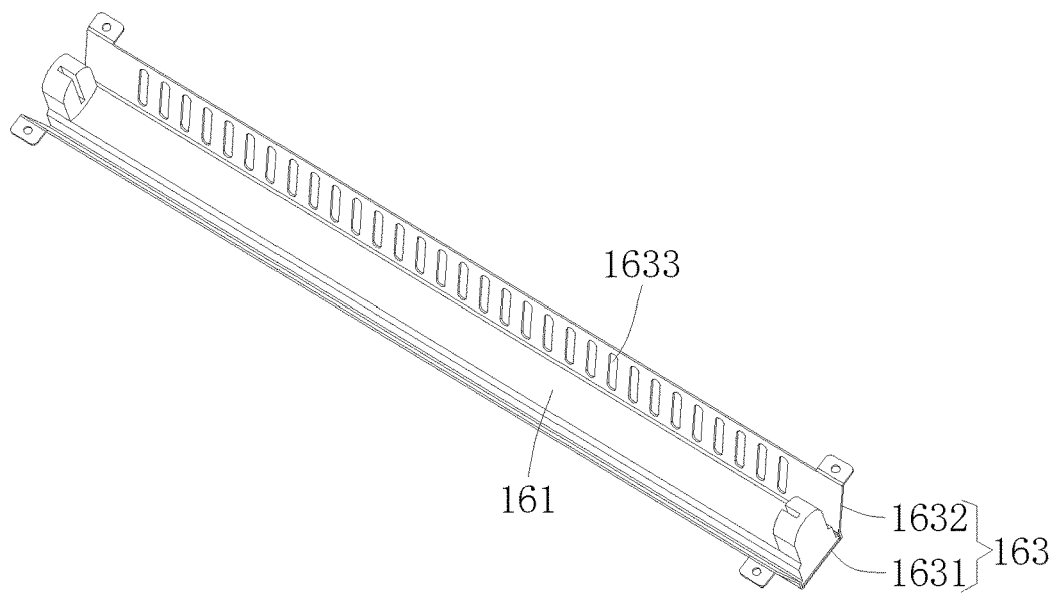
FIG. 5 is a schematic diagram of the reflector and lampholder in FIG. 4.

In one embodiment, referring to FIGS. 3, 4, and 5, an airflow hole 1633 is arranged on the side of the reflector 163 close to the fan 13 so that after air enters the reflector 163, it is easier to enter the fan 13 from the airflow hole 1633 to reduce air resistance. Of course, in other embodiments, airflow holes 1633 may be arranged on both sides of the reflector 163, respectively. In some other embodiments, an airflow hole 1633 may be arranged on the side of the reflector 163 away from the fan 13.

In one embodiment, the UV tube 162 can be detachably installed on the lampholder 161 so as to replace the UV tube 162.

In one embodiment, referring to FIGS. 4 to 5, the reflector 163 includes two reflective side plates 1632 and a supporting plate 1631, and the airflow hole 1633 is arranged on the reflective side plate 1632. The supporting plate 1631 is connected to the upper side of the two reflective side plates 1632, that is, the supporting plate 1631 is connected to the side of the two reflective side plates 1632 away from the window 114. When in use, the two reflective side plates 1632 are located on both sides of the ultraviolet light source to reflect light. The distance between the two reflective side plates 1632 is gradually expanded from the supporting plate 1631 to the direction away from the supporting plate 1631, so that on the one hand, the light emitted by the ultraviolet light source can be reflected, and the reflected light can also be guaranteed to cover a larger area.

In one embodiment, the reflector 163 can be stamped from a metal plate to facilitate processing and manufacture. In addition, the reflector 163 can also cool the ultraviolet light source. Of course, in some embodiments, the reflector 163 may also be a plastic cover, and a reflective coating is arranged on the inner surface of the plastic cover.

In one embodiment, when the ultraviolet light source is UV tube 162 and main machinery 10 also includes lampholder 161, two reflective side plates 1632 are located on both sides of lampholder 161, and when UV tube 162 is installed on lampholder 161, two reflective side plates 1632 are located on both sides of UV tube 162 to reflect light. The distance between the two reflective side plates 1632 is gradually expanded from the supporting plate 1631 to the direction away from the supporting plate 1631, so that on the one hand, the light emitted by the UV tube 162 can be reflected, and the reflected light can also be guaranteed to cover a larger area.

In one embodiment, the lower end of the reflective side plate 1632 may be fixed to the bottom of the housing 11, that is, the end of the reflective side plate 1632 away from the supporting plate 1631 is fixed to the bottom of the housing 11 to install the reflector 163 in the housing 11.

In one embodiment, the supporting plate 1631 of the reflector 163 can be fixedly connected to the lampholder 161, and the lampholder 161 is fixed in the housing 11 to support the reflector 163 by the lampholder 161.

In some other embodiments, the lower end of the reflective side plate 1632 can be fixed to the bottom of the housing 11, and the supporting plate 1631 of the reflector 163 can be fixedly connected to the lampholder 161 to ensure the installation stability of the reflector 163.

In one embodiment, referring to FIGS. 3 and 4, the fan 13 includes fan cover 131, tubular wind turbine 132, and electrical machinery 133. Electrical machinery 133 is connected to tubular wind turbine 132 to drive tubular wind turbine 132 to rotate through electrical machinery 133, and tubular wind turbine 132 is installed in the fan cover 131, airflow is guided by fan cover 131. Using the tubular wind turbine 132, the volume can be made smaller, and the air volume can be large, and the main machinery 10 can be made smaller in size. Of course, in other embodiments, other fan 13 structures can also be used.

In one embodiment, heater 12 is located between fan 13 and reflector 163, and heater 12 is located at the entrance of fan 13, so that after the air is preheated by reflector 163 and enters heater 12 for heating, and then enters fan 13. This structure can better heat the air and increase energy utilization rate, and the heater 12 power can be made smaller.

In one embodiment, please refer to FIGS. 3 to 4, the bottom of housing 11 is provided with air inlet 115, which is located at the corresponding position of heater 12, so that part of the air will pass through reflector 163 to fan 13, and the other part of air can directly enter heater 12 from the bottom of housing 11 for heating in order to reduce the air resistance and to ensure that fan 13 has sufficient air output.

Figure 6:
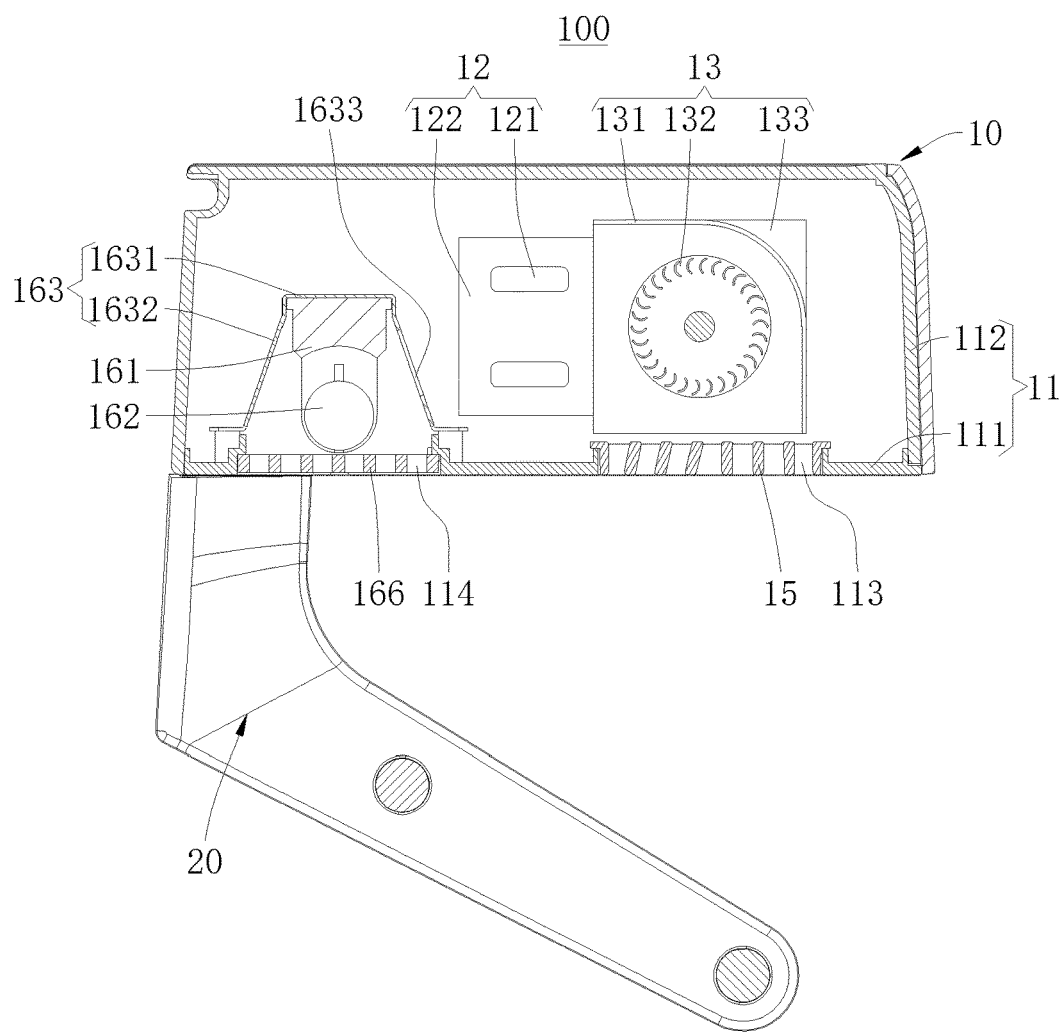
FIG. 6 is a schematic cross-sectional view of the towel disinfection dryer provided by the second embodiment of the present application.

In one embodiment, please refer to FIG. 6, the bottom of housing 11 is not provided with air inlet 115, and the air needs to pass through reflector 163 before it can enter fan 13.

In an embodiment, please refer to FIGS. 3 to 4, main machinery 10 also includes a grilling window 166, the grilling window 166 is detachably installed at the bottom of housing 11 and the grilling window 166 covers window 114 to protect UV tube 162 in reflector 163. And light transmitting and ventilation could be achieved by grilling window 166.

In one embodiment, the grilling window 166 may use a light-transmitting material, so that the light emitted by the UV tube 162 can be transmitted through the grilling window 166 to improve the utilization of light.

In one embodiment, the heater 12 includes a heating plate 121 and a plurality of cooling fins 122, and the plurality of cooling fins 122 are arranged on the heating plate 121 to heat the air more efficiently and quickly. The use of heating plate 121 has high safety. Of course, in other embodiments, heater 12 can also use heating wires, heating tubes, etc.

In one embodiment, the main machinery 10 also includes a ventilation window 15, which is installed in the air outlet 113 to guide the airflow to diffuse, that is, when the airflow blown by the fan 13 passes through the ventilation window 15, it is guided and diffused by the ventilation window 15 to better perform the cloth heating and drying.

In one embodiment, shutters may be used for ventilation window 15. In some other embodiments, the ventilation window 15 can also use a guide plate to guide the airflow to diffuse.

Figure 8:
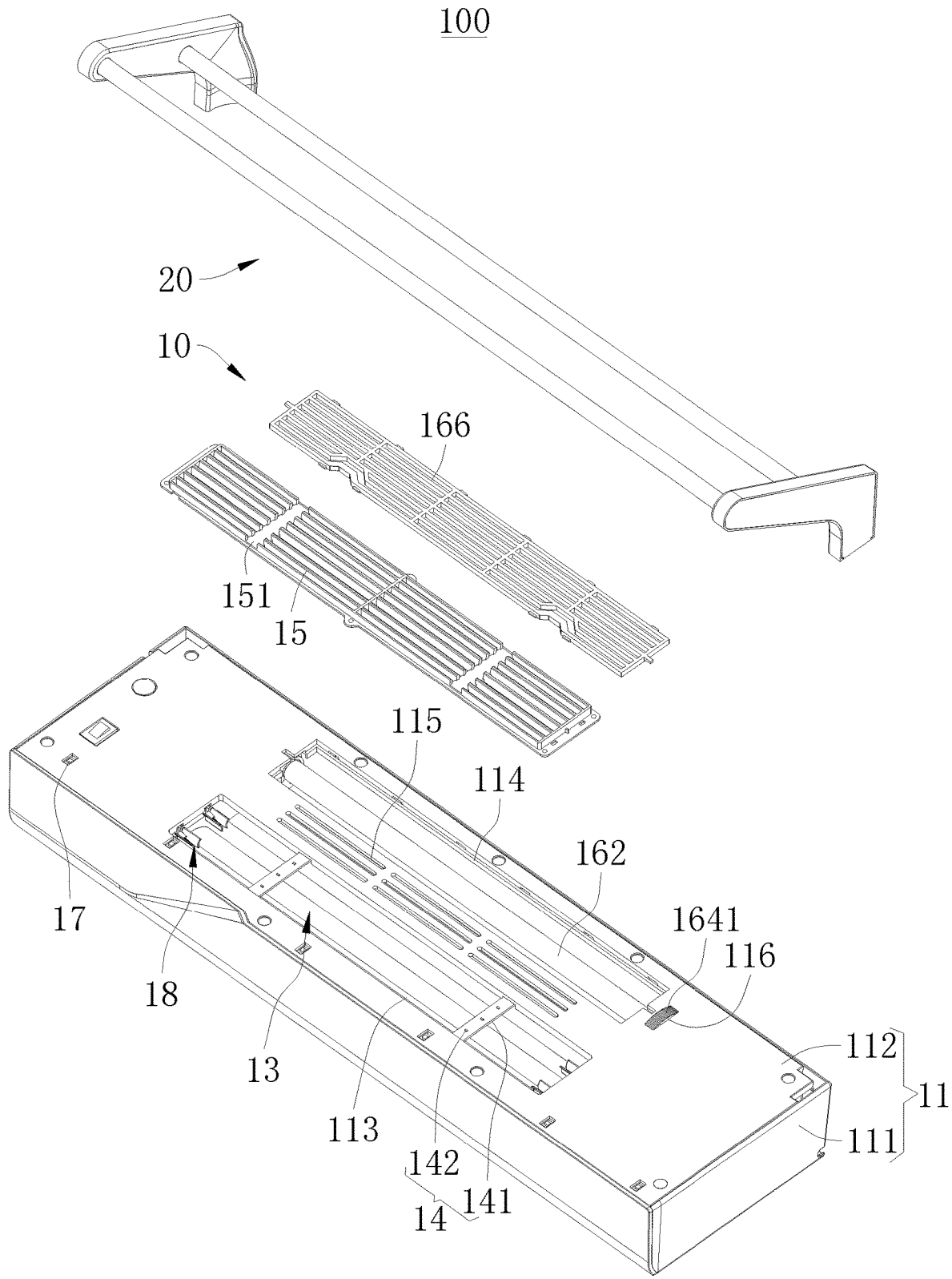
FIG. 8 is a schematic diagram of an exploded structure of the towel disinfection dryer provided by the third embodiment of the present application.
Figure 9:
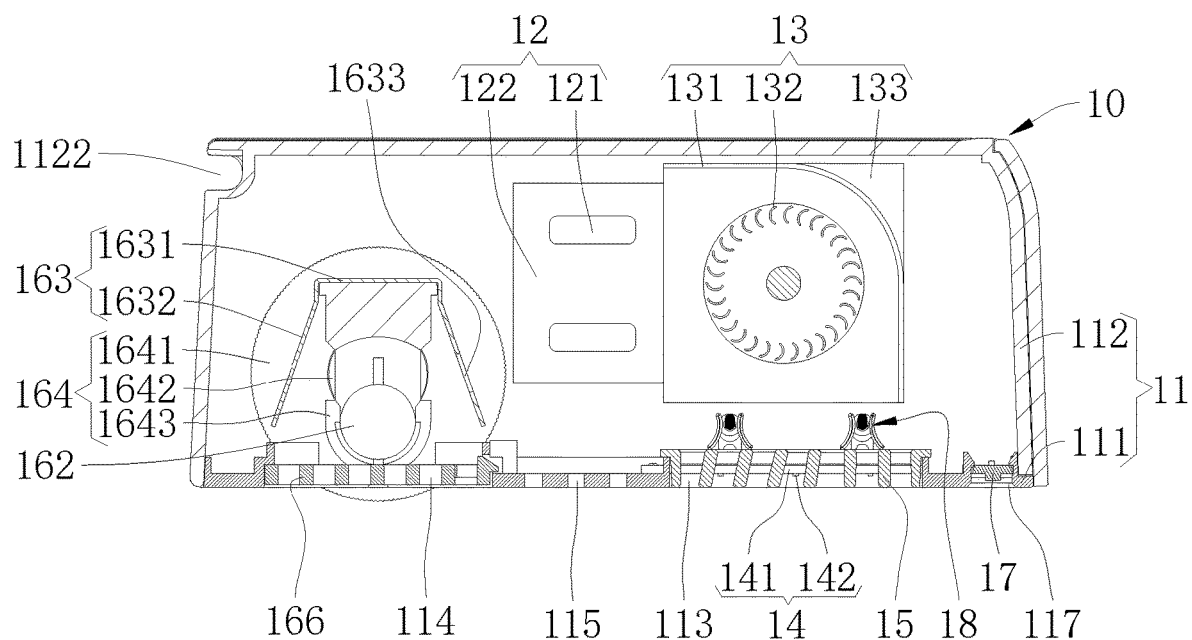
FIG. 9 is a schematic cross-sectional view of the main machinery in FIG. 8.
Figure 10:
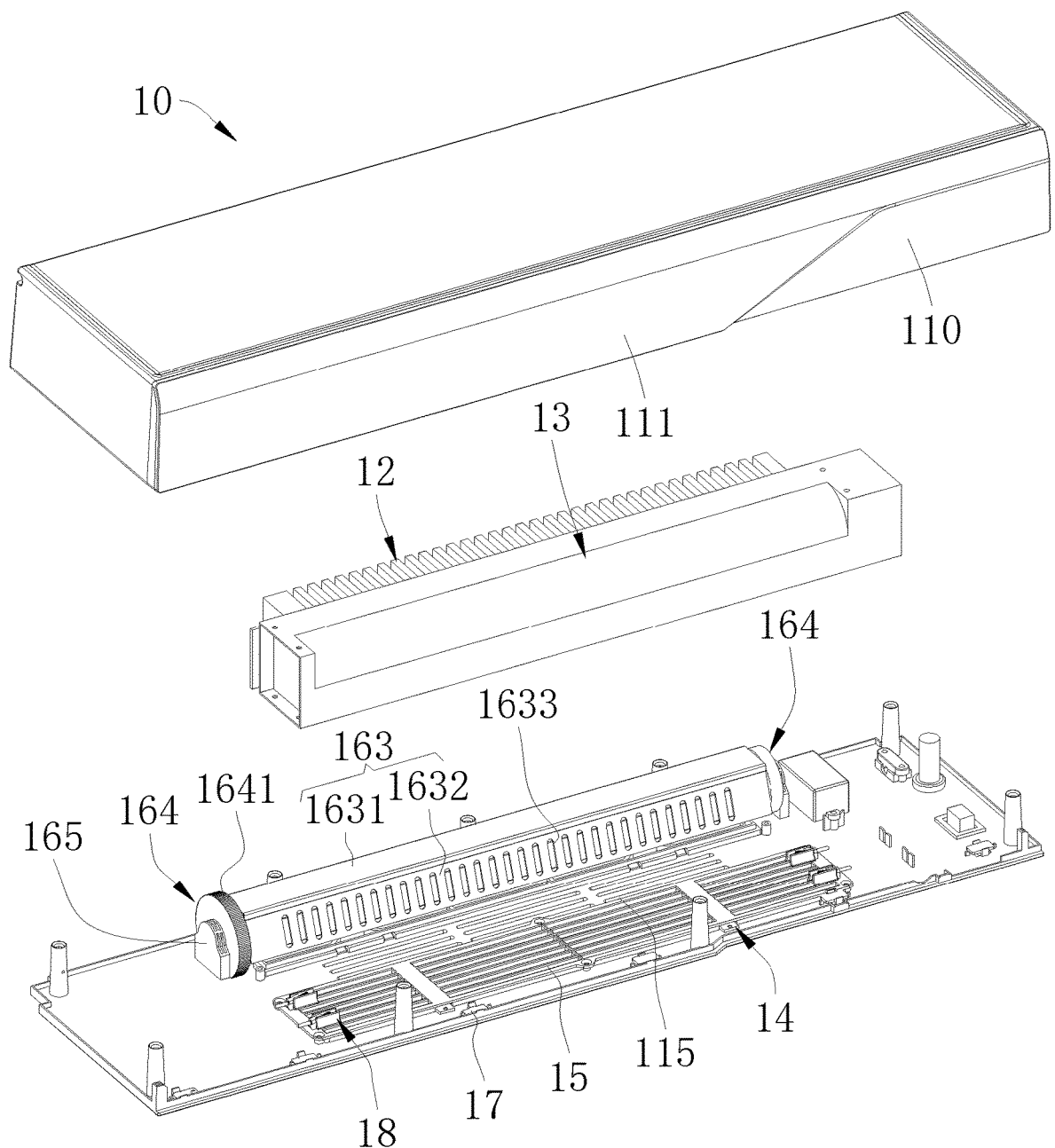
FIG. 10 is a first schematic diagram of the explosive structure of the main machinery in FIG. 8.

In one embodiment, please refer to FIGS. 8 to 10, the main machinery 10 further includes two turnplates 164 and two supporting seats 165. The two ends of lampholder 161 are respectively connected to two turnplate 164, and the reflector 163 is supported on turnplate 164. For example, the reflector 163 can be fixed on lampholder 161, or both ends of reflector 163 can be connected to two turnplate 164, so that the lampholder 161 and the reflector 163 can be supported by two turnplate 164. The two turnplates 164 are installed on the two supporting seats 165 respectively, and the two supporting seats 165 are installed in the housing 11 respectively to support the turnplate 164 in the housing 11. The turnplate 164 is arranged to support lampholder 161 and reflector 163. The turnplate 164 can be rotated to drive lampholder 161, UV tube 162 and reflector 163 to rotate, thereby adjusting the angle of the UV tube 162 emitting ultraviolet light and the reflector 163 reflecting ultraviolet light, and further adjusting the UV tube 162 coverage area to disinfect the designated area.

Figure 11:
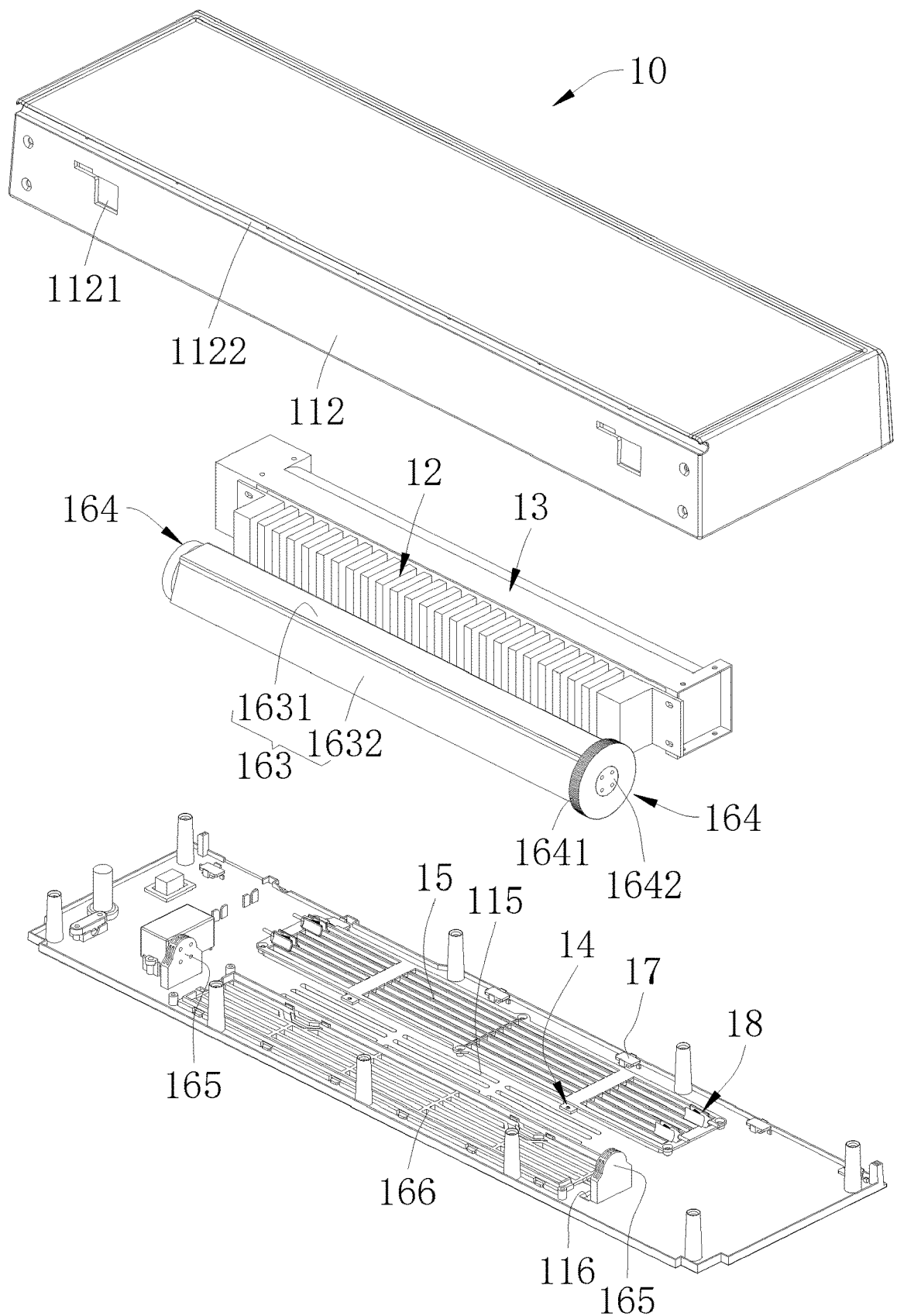
FIG. 11 is a second schematic diagram of the exploded structure of the main machinery in FIG. 8.
Figure 12:
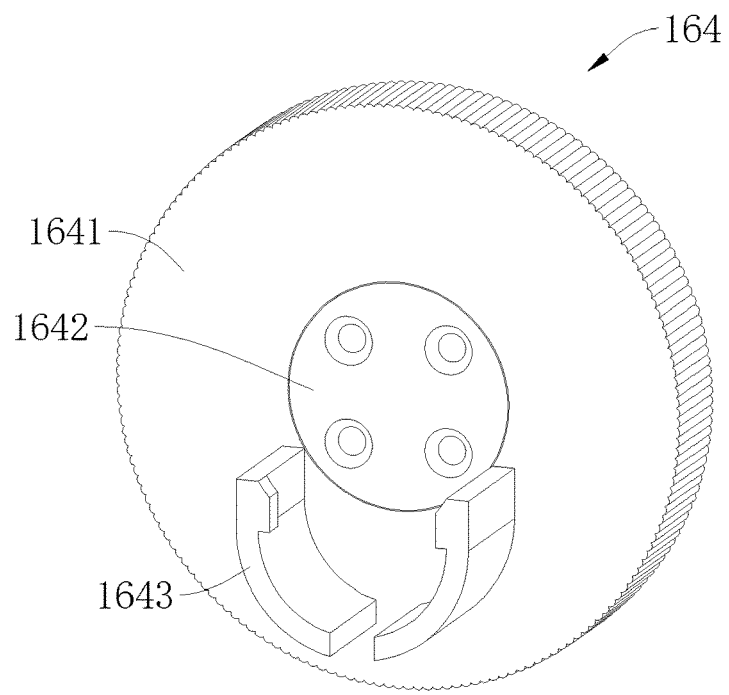
FIG. 12 is a schematic diagram of the turnplate in FIG. 11.

In one embodiment, referring to FIGS. 9, 11 and 12, part of the side of the turnplate 164 protrudes from the housing 11, and the bottom of the housing 11 is provided with an opening 116 for part of the side of the turnplate 164 to protrude, so as to facilitate the rotation of the turnplate 164. In this embodiment, the diameter of a turnplate 164 can be setup to be larger, so that part of the side of the turnplate 164 protrudes from the bottom of the housing 11 to facilitate the rotation of the turnplate 164. In other embodiments, the opening 116 may be provided on the positions of the housing 11 corresponding to the two turnplates 164, and part of the side surfaces of the two turnplates 164 respectively extend out of the bottom surface of the housing 11, so that the lampholder 161 can be rotated more stably.

In one embodiment, referring to FIG. 12, the turnplate 164 includes a pivot 1642 and a rotary disk 1641, the rotary disk 1641 is rotatably installed on the pivot 1642, the pivot 1642 is installed on the supporting seat 165, the lampholder 161 and the reflector 163 are arranged on the rotary disk 1641, so that the rotary disk 1641 is rotatably supported by the pivot 1642. When the rotary disk 1641 rotates, it can drive the lampholder 161, UV tube 162 and reflector 163 to rotate. In other embodiments, a disk can also be used as the turnplate 164, and the disk is rotatably installed on the supporting seat 165. In some other embodiments, the turnplate 164 can be driven to rotate by a rotating motor, and then the lampholder 161 and the reflector 163 can be driven to rotate by the rotating motor to adjust the UV tube 162 coverage area.

In one embodiment, a damping member, such as a friction block, may be arranged in the housing 11, and the turnplate 164 abuts the damping member to position the turnplate 164, and then after the turnplate 164 is rotated, the turnplate 164 is positioned. Of course, a turnplate 164 with a friction plate can also be used to position the turnplate 164. In some other embodiments, marbles may be arranged to abut the turnplate 164, and then after the turnplate 164 is rotated, the turnplate 164 is positioned.

In one embodiment, the rotary disk 1641 is further provided with a deck 1643, which is used to clamp and fix the lampholder 161, that is, the lampholder 161 can be clamped in the deck 1643, and then the lampholder 161 and the rotary disk 1641 are connected to facilitate assembly.

Figure 7:
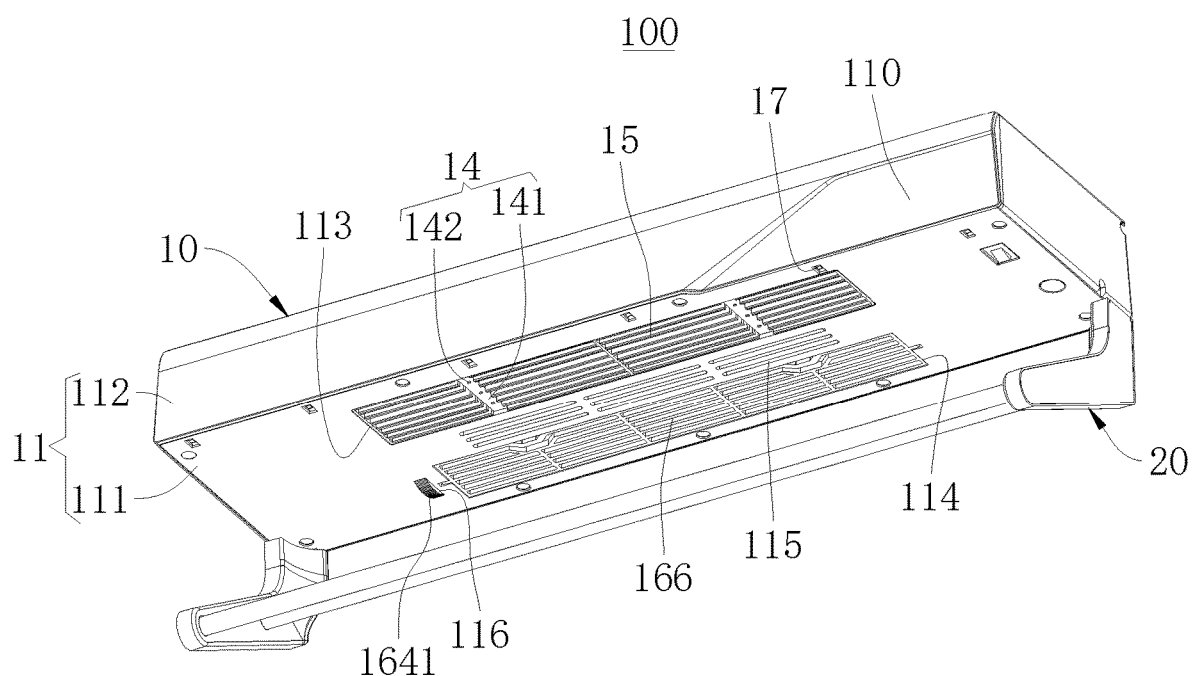
FIG. 7 is a schematic diagram of a towel disinfection dryer provided by the third embodiment of the present application.

In one embodiment, referring to FIGS. 7 to 9, the main machinery 10 further includes an ultraviolet LED module 114, and the ultraviolet LED module 114 is installed at the bottom of the housing 11 to support the ultraviolet LED module 114 through the housing 11. The ultraviolet LED module 114 is arranged at the position corresponding to the air outlet 113, and the air blown by fan 13 passes through the air outlet 113, which can take away the heat generated by the ultraviolet LED module 114, thereby cooling the ultraviolet LED module 114 and ensuring the service life of the ultraviolet LED module 114; And the airflow generated by fan 13 will blow to the fabric under main machinery 10, so that the heat generated by ultraviolet LED module 114 can be brought to the fabric under main machinery 10, so as to utilize the heat generated by ultraviolet LED module 114 and the heat generated by heater 12 together to heat and dry the fabric pieces to improve energy utilization. In addition, the ultraviolet LED module 114 is arranged at the position corresponding to the air outlet 113, and the ultraviolet light generated by the ultraviolet LED module 114 can better cover the corresponding area under the air outlet 113, so that the cloth under the air outlet 113 can be dried and disinfected at the same time.

In one embodiment, referring to FIGS. 7-9, the ultraviolet LED module 114 includes a base plate 141 and an ultraviolet LED bead 142, the base plate 141 is installed at the bottom of the housing 11, the base plate 141 is supported in the air outlet 113, and the ultraviolet LED bead 142 is installed on the base plate 141 to support and control the ultraviolet LED bead 142 through the base plate 141, so that the ultraviolet LED bead 142 emits ultraviolet light to sterilize the cloth. Due to the relatively small size of ultraviolet LED module 114, the corresponding space in housing 11 is also small, and housing 11 can be made smaller, and the location layout of ultraviolet LED module 114 can be facilitated, which can control the covering area of the ultraviolet light emitted by ultraviolet LED module 114. Using ultraviolet LED module 114, it can save more energy, and is easy to install and fix, which can simplify the structure of main machinery 10, facilitate assembly, and facilitate the processing and production of main machinery 10.

In one embodiment, the base plate 141 is arranged in a long strip shape, which is convenient to support at the air outlet 113, and can reduce the occupied area of the base plate 141, facilitate the heat dissipation of the base plate 141 by the airflow, and can also reduce the resistance of the base plate 141 to the airflow, which is convenient for the airflow to heat and dry the cloth under the main machinery 10. Of course, in some other embodiments, the base plate 141 can also be arranged in other shapes, such as a circle, a square, and so on. In some other embodiments, the base plate 141 may also be arranged in a ring or frame shape, so that a hole structure is formed in the base plate 141, or holes are directly arranged on the base plate 141 to allow air flow to pass.

In one embodiment, a plurality of ultraviolet LED modules 114 makes that the power of a single ultraviolet LED module 114 can be relatively small, which can reduce the heat generated by each ultraviolet LED module 114 and facilitate the heat dissipation of each ultraviolet LED module 114. The service life of each ultraviolet LED module 114 is guaranteed, and the position of each ultraviolet LED module 114 can be conveniently arranged to increase the area covered by ultraviolet light. Of course, in some embodiments, the ultraviolet LED module 114 can be single one.

In one embodiment, when there is a plurality of ultraviolet LED modules 114, the base plates 141 of the plurality of ultraviolet LED modules 114 are arranged at intervals along the longitudinal direction of the air outlet 113, that is, the longitudinal direction of each base plate 141 is perpendicular or slightly inclined to the longitudinal direction of the air outlet 113. In this way, the length of each base plate 141 can be made shorter to ensure the strength of each ultraviolet LED module 114, and it is also convenient to support at the air outlet 113. In other embodiments, when there is a plurality of ultraviolet LED modules 114, the base plates 141 of the plurality of ultraviolet LED modules 114 are arranged at intervals along the width direction of the air outlet 113, that is, the longitudinal direction of each base plate 141 is perpendicular or slightly inclined to the width of the air outlet 113 In this way, the base plate 141 can be made longer and the number of ultraviolet LED modules 114 can be reduced.

In one embodiment, each base plate 141 is provided with a plurality of the ultraviolet LED bead 142, so that the power of each ultraviolet LED bead 142 can be made smaller, which can reduce the heat generated by each ultraviolet LED bead 142, facilitate the heat dissipation of each ultraviolet LED bead 142, ensure the service life of each ultraviolet LED bead 142 and facilitate the layout of the position of each ultraviolet LED bead 142 so as to increase the area covered by ultraviolet light. Of course, in some embodiments, there may be one ultraviolet LED bead 142 on the base plate 141.

In one embodiment, the ventilation window 15 defines an accommodating slot 151 and the ultraviolet LED module 114 is arranged in the accommodating slot 151, that is, the position of the ventilation window 15 corresponding to the ultraviolet LED module 114 is provided with an accommodating slot 151 to support the ultraviolet LED module 114, and to reduce the volume of main machinery 10. In some embodiments, the ultraviolet LED module 114 can also be arranged under the ventilation window 15. Of course, in other embodiments, the ultraviolet LED module 114 can also be arranged above the ventilation window 15.

In an embodiment, please refer to FIGS. 7-9, the window 114 is located at the position corresponding to the rear side of the bottom of the housing 11, so that when in use, the window 114 is closer to the wall, so that the UV tube 162 is also closer to the wall to better restrict the range of ultraviolet light and to enhance the safety.

In one embodiment, a buckle 1121 is provided on the rear side of the housing 11, so that the housing 11 can be installed on the wall by means of hooking, which is convenient for installation and fixation. Of course, in some other embodiments, the housing 11 can also be installed on the wall using screws.

In one embodiment, trunking 1122 is provided on the rear side of housing 11 so that the power supply can be arranged in trunking 1122.

In one embodiment, referring to FIGS. 8 to 10, an ultraviolet LED module 217 is provided on the side of the fan cover 131 away from the heater 12 to increase the coverage area of the ultraviolet light, and when the air flows out through the air outlet 113 to form a siphon effect so that the hot air at the ultraviolet LED module 217 is sucked away to form air flow, and the ultraviolet LED module 217 is cooled. After the heat generated by the ultraviolet LED module 217 is sucked away and discharged through the air outlet 113 for drying, thereby improving energy utilization.

In one embodiment, the ultraviolet LED module 217 is installed inside the housing 11, and an optical aperture 117 is opened at the bottom of the housing 11 to allow the ultraviolet light generated by the ultraviolet LED module 217 to pass through. Of course, in other embodiments, the ultraviolet LED module 217 may be installed outside the housing 11, such as on the bottom surface of the housing 11.

In one embodiment, please refer to FIGS. 9 to 11, main machinery 10 also includes a negative ion generator (not shown), the negative ion generator has emitter head 18, the emitter head 18 of the negative ion generator is arranged at the position corresponding to air outlet 113, so that after passing through the emitter head 18 of the negative ion generator, the air flow generated from fan 13 flows out of the air outlet 113 to form an air flow with negative ions, and the cloth is then sterilized by the negative ions to improve the disinfection performance.

Figure 13:
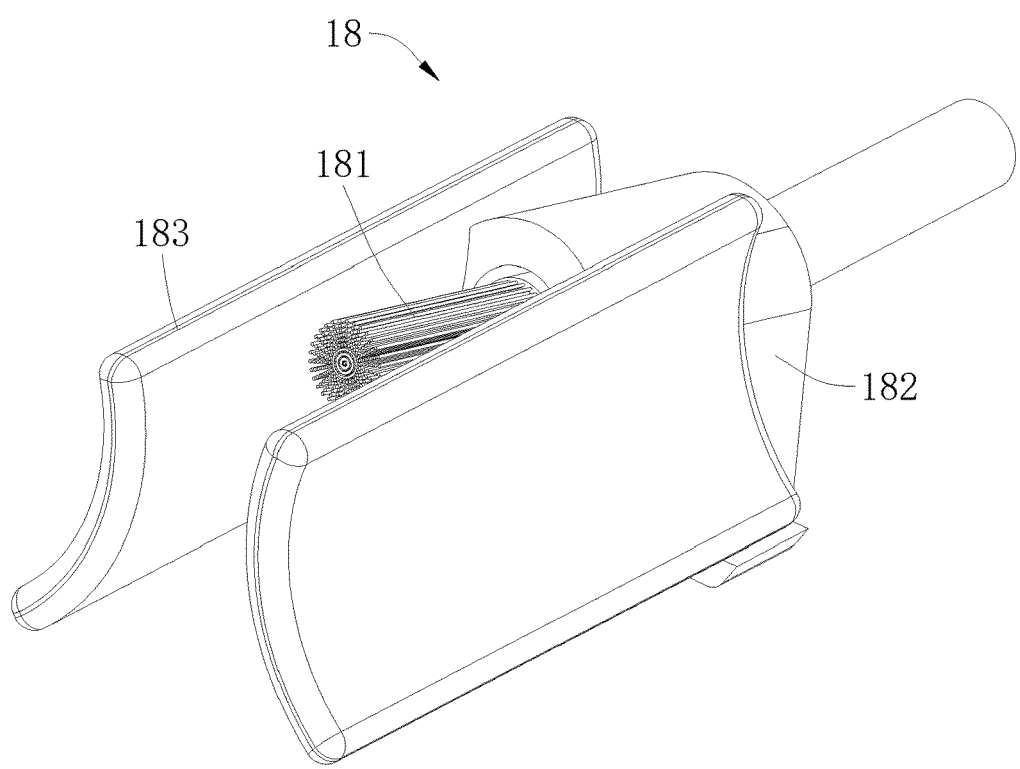
FIG. 13 is a schematic diagram of an emitter head provided by an embodiment of the present application.
Figure 14:
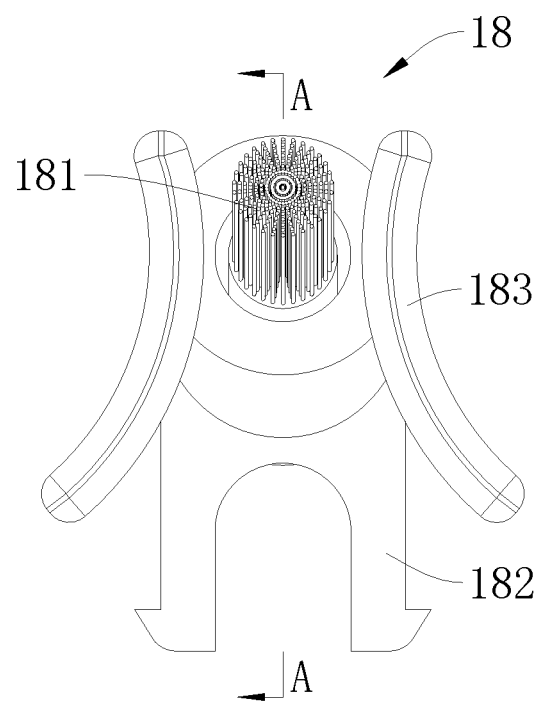
FIG. 14 is a schematic diagram of the front view of the emitter head in FIG. 13.

In one embodiment, referring to FIG. 11, FIG. 13 and FIG. 14, the emitter head 18 includes a negative ion release brush 181, a holder 182, and two guide plates 183. The holder 182 is installed on housing 11, the negative ion release brush 181 is installed on holder 182, and the negative ion release brush 181 is supported by the support, and the negative ion release brush 181 is extended to air outlet 113. Two guide plates 183 are respectively arranged on the opposite side of negative ion release brush 181 on both sides, the distance between the two guide plates 183 gradually expands from the middle of the guide plate 183 downwards, that is, the distance between the two guide plates 183 is gradually expanded from the middle of the guide plate 183 to the lower side of the guide plate 183, so that the space between the lower part of the two guide plates 183 gradually increases, and the air flow to the lower part of the two guide plates 183 will slow down and diffuse, so that the negative ions in the air flow can be better diffused to increase the area covered by the negative ions.

Figure 15:
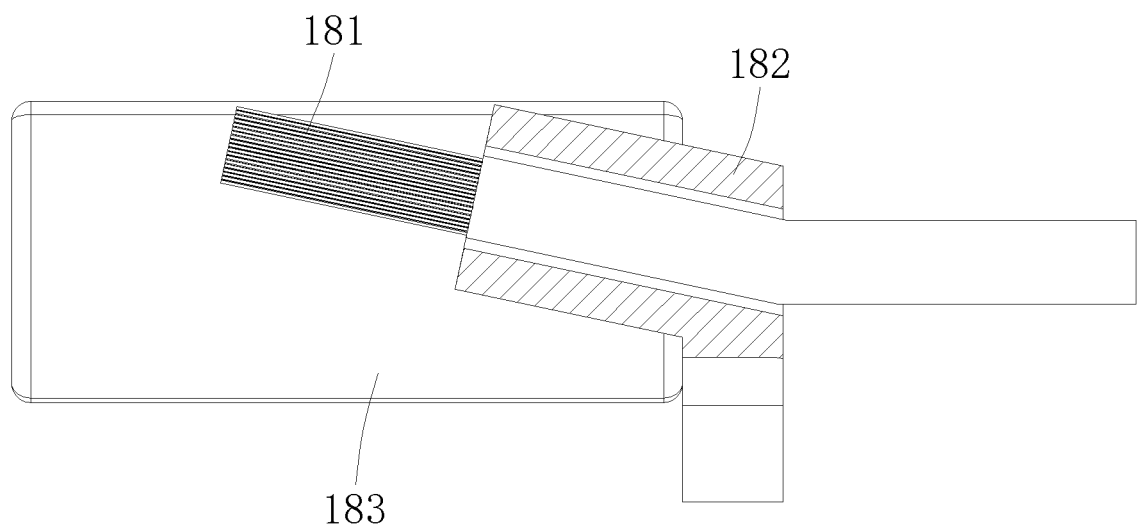
FIG. 15 is a schematic sectional view of the structure taken along the line A-A in FIG. 14.

In one embodiment, referring to FIGS. 13 to 15, the guide plate 183 is fixedly connected to the holder 182 to facilitate the installation and fixation of the guide plate 183, and further facilitate the installation and fixation of the emitter head 18. Of course, in some embodiments, the guide plate 183 may also be separately supported in the housing 11.

In one embodiment, the distance between the two guide plates 183 is gradually expanded upward from the middle of the guide plate 183, that is, the distance between the two guide plates 183 is gradually expanded from the middle of the guide plate 183 to the upper side of the guide plate 183 so that more air enters between the two guide plates 183, making more air contact the negative ion release brush 181 to generate more negative ions.

In one embodiment, the distance between the upper sides of the two guide plates 183 is less than the distance between the lower sides of the two guide plates 183 to ensure that the air flow velocity from the lower sides of the two guide plates 183 is less than that of the air flow outside the two guide plates 183. Speed, this will form a certain siphon effect on the underside of the two guide plates 183 to better diffuse the negative ions in the airflow flowing out between the two guide plates 183, thereby increasing the area covered by the negative ions.

In one embodiment, the negative ion release brush 181 is located at a corresponding position above the middle of the guide plate 183, so that more air flow passes through the negative ion release brush 181, and is guided and diffused by the guide plate 183.

In one embodiment, the negative ion release brush 181 extends obliquely upward, that is, the negative ion release brush 181 extends obliquely upward from the holder 182 to the free end of the negative ion release brush 181. Since the free end of the negative ion release brush 181 is relatively more open, extending the negative ion release brush 181 obliquely upwards can reduce the resistance of the negative ion release brush 181 to the air flow, thereby facilitating the air flow through the negative ion release brush 181 to produce more negative ions.

In one embodiment, each guide plate 183 is arranged in an arc shape to guide the air flow more smoothly.

In one embodiment, please refer to FIG. 11, both ends of the air outlet 113 in the longitudinal direction are respectively provided with emitter heads 18 so that the negative ions generated by the emitter head 18 can cover a larger area in order to better disinfect the cloth under the main machinery 10.

In one embodiment, along the width direction of the air outlet 113, a plurality of emitter heads 18 are provided at both ends of the longitudinal direction of the air outlet 113, respectively to increase the negative ions to cover a larger area, so as to better perform cloth disinfection under the main machinery 10.

Figure 16:
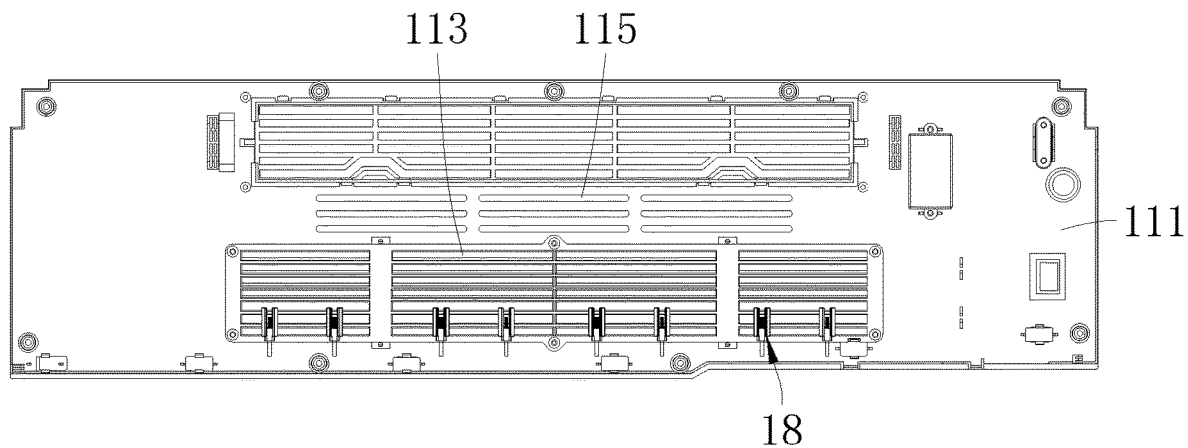
FIG. 16 is a schematic diagram of the layout structure of the emitter head provided by the fourth embodiment of the present application.

In one embodiment, please refer to FIG. 16, the air outlet 113 is provided with a plurality of emitter heads 18 on the side in the longitudinal direction, so that the negative ions generated by the emitter head 18 can cover a larger area, so as to better disinfect the cloth under the main machinery 10.

In one embodiment, a plurality of emitter heads 18 may be arranged on one side of the length of the air outlet 113, so that the negative ions generated by the emitter head 18 can cover the entire length of the air outlet 113, so as to better sterilize the cloth under the main machinery 10.

Figure 17:
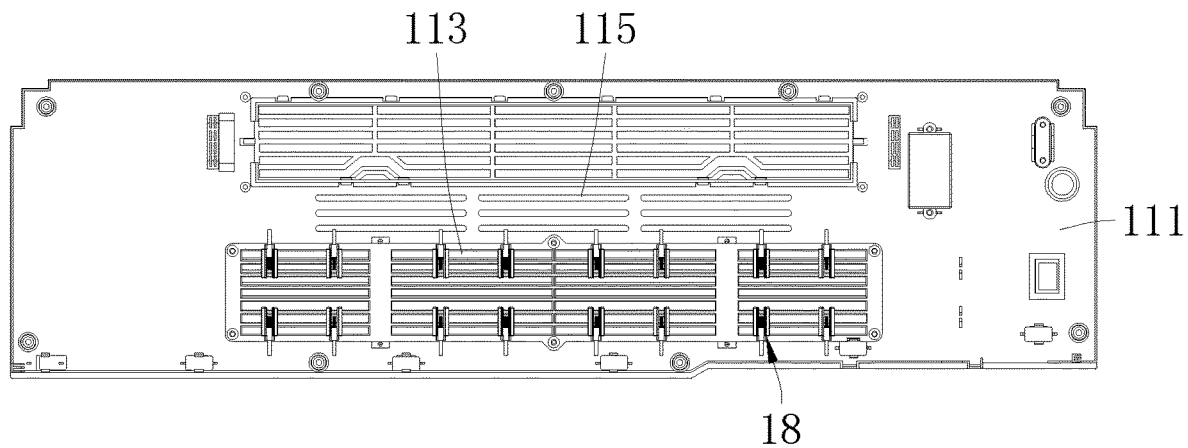
FIG. 17 is a schematic diagram of the layout structure of the emitter head provided by the fifth embodiment of the present application.

In one embodiment, please refer to FIG. 17, a plurality of emitter heads 18 are arranged on both sides of the length direction of the air outlet 113, so that the negative ions generated by the emitter head 18 can cover the entire air outlet 113, so as to better sterilize the cloth under the main machinery 10.

The towel disinfection dryer 100 of the embodiments of the present application is of small size, large air volume, low energy consumption, high energy utilization, and long service life.

The above descriptions are only optional embodiments of the present application and are not used to limit the present application. Any modification, equivalent replacement and improvement made within the spirit and principles of the present application shall be included in the scope of protection of the present application.

What is claimed is:

1. A towel disinfection dryer, comprising a main machinery, wherein the main machinery comprises a housing, an ultraviolet light source installed in the housing, a reflector arranged above the ultraviolet light source, a heater installed in the housing, and a fan installed in the housing, the reflector is installed in the housing, the bottom of the housing is provided with a window exposing the ultraviolet light source, and the bottom of the housing corresponding to the outlet of the fan is provided with an air outlet, the heater is arranged on the airflow path of the fan, the reflector defines one or more airflow holes, and the reflector is arranged on the airflow path of the fan;
wherein the main machinery further comprises two turnplates for driving the lampholder to rotate and two supporting seats for supporting the two turnplates respectively, the two supporting seats are installed in the housing, the ultraviolet light source is a UV tube, the two ends of the lampholder are installed on the two turnplates respectively, and the reflector is supported on the turnplate.

2. The towel disinfection dryer of claim 1, wherein the reflector defines one or more airflow holes on the side close to the fan.

3. The towel disinfection dryer of claim 1, wherein the reflector comprises a reflective side plate arranged on both sides of the ultraviolet light source and a supporting plate connected to the two reflective side plates on the side away from the window, the distance between the two reflective side plates is gradually expanded from the supporting plate to a direction away from the supporting plate, and the airflow hole is arranged on the reflective side plate.

4. The towel disinfection dryer of claim 1, wherein part of the side surface of the turnplate protrudes from the bottom of the housing, and the bottom of the housing defines an opening from which the part of the side face of the turnplate protrudes.

5. The towel disinfection dryer of claim 1, wherein the turnplate comprises a pivot installed on the supporting seat and a rotary disk installed on the pivot, and the corresponding end of the lampholder is connected to the rotary disk, and the reflector is supported on the rotary disk.

6. The towel disinfection dryer of claim 5, wherein the rotary disk is further provided with a deck, and the corresponding end of the lampholder is clamped in the deck.

7. The towel disinfection dryer of claim 1, wherein the fan includes a fan cover installed in the housing, a tubular wind turbine installed in the fan cover and an electrical machinery driving the wind turbine to rotate.

8. The towel disinfection dryer of claim 1, wherein the heater is arranged between the fan and the reflector, and the heater is arranged at the entrance of the fan.

9. The towel disinfection dryer of claim 8, wherein an air inlet is arranged at the bottom of the housing corresponding to the heater.

10. The towel disinfection dryer of claim 1, wherein the main machinery further comprises an ultraviolet LED module, and the ultraviolet LED module is arranged at a position corresponding to the air outlet.

11. The towel disinfection dryer of claim 10, wherein the ultraviolet LED module 1 comprises a long base plate and an ultraviolet LED bead installed on the base plate, and the base plate is supported in the air outlet.

12. The towel disinfection dryer of claim 1, wherein the main machinery further comprises a negative ion generator installed in the housing, the negative ion generator has an emitter head, and the emitter head is arranged at the position corresponding to the air outlet.

13. The towel disinfection dryer of claim 12, wherein the emitter head comprises a negative ion release brush arranged at the air outlet, a holder supporting the negative ion release brush, and two guide plates for guiding the diffusion of airflow, the holder is installed in the housing, and the two guide plates are arranged on opposite sides of the negative ion release brush respectively, and the distance between the two guide plates is gradually expanded from the middle of the guide plate to the lower side of the guide plate.

14. The towel disinfection dryer of claim 13, wherein the distance between the two guide plates is gradually expanded from the middle of the guide plate to the upper side of the guide plate.

15. The towel disinfection dryer of claim 13, wherein the distance between the upper sides of the two guide plates is smaller than the distance between the lower sides of the two guide plates.

16. The towel disinfection dryer of claim 13, wherein the negative ion release brush is arranged in the middle of the guide plate close to the position corresponding to the upper side of the guide plate.

17. The towel disinfection dryer of claim 13, wherein the negative ion release brush extends obliquely upward from the holder to the free end of the negative ion release brush.

18. The towel disinfection dryer of claim 13, wherein both ends of the longitudinal direction of the air outlet are provided with the emitter head respectively; or the side of the longitudinal direction of the air outlet is provided with a plurality of the emitter heads.

19. The towel disinfection dryer of claim 1, wherein the towel disinfection dryer further comprises a rack for hanging cloth, and the rack is supported on the bottom of the housing.

20. A towel disinfection dryer, comprising a main machinery, wherein the main machinery comprises a housing, an ultraviolet light source installed in the housing, a reflector arranged above the ultraviolet light source, a heater installed in the housing, and a fan installed in the housing, the reflector is installed in the housing, the bottom of the housing is provided with a window exposing the ultraviolet light source, and the bottom of the housing corresponding to the outlet of the fan is provided with an air outlet, the heater is arranged on the airflow path of the fan, the reflector defines one or more airflow holes, and the reflector is arranged on the airflow path of the fan;

wherein the heater is arranged between the fan and the reflector, and the heater is arranged at the entrance of the fan.

\* \* \* \* \*